(12) United States Patent
Pattison et al.

(10) Patent No.: US 11,627,989 B2
(45) Date of Patent: Apr. 18, 2023

(54) PROTECTIVE SHEATH FOR USE WITH A SURGICAL INSTRUMENT HAVING AN EXPANDABLE BODY

(71) Applicant: Covidien LP, Mansfield, MA (US)

(72) Inventors: Douglas M. Pattison, East Hartford, CT (US); Oksana Buyda, East Haven, CT (US); Amanda M. Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/847,842

(22) Filed: Apr. 14, 2020

(65) Prior Publication Data

US 2021/0315612 A1 Oct. 14, 2021

(51) Int. Cl.
*A61B 17/34* (2006.01)
*A61B 17/00* (2006.01)

(52) U.S. Cl.
CPC ...... *A61B 17/3496* (2013.01); *A61B 17/3423* (2013.01); *A61B 2017/00557* (2013.01); *A61B 2017/00862* (2013.01)

(58) Field of Classification Search
CPC ............ A61B 17/3421; A61B 17/3423; A61B 17/3496
See application file for complete search history.

(56) References Cited

U.S. PATENT DOCUMENTS

| | | |
|---|---|---|
| 5,073,169 A | 12/1991 | Raiken |
| 5,137,520 A | 8/1992 | Maxson et al. |
| 5,147,316 A | 9/1992 | Castillenti |
| 5,176,648 A | 1/1993 | Holmes et al. |
| 5,226,890 A | 7/1993 | Ianniruberto et al. |
| 5,290,249 A | 3/1994 | Foster et al. |
| 5,300,033 A | 4/1994 | Miller |
| 5,330,497 A | 7/1994 | Freitas et al. |
| 5,366,446 A | 11/1994 | Tal et al. |
| 5,403,336 A | 4/1995 | Kieturakis et al. |
| 5,484,420 A | 1/1996 | Russo |
| 5,713,869 A | 2/1998 | Morejon |
| 5,792,112 A | 8/1998 | Hart et al. |
| 5,830,232 A | 11/1998 | Hasson |
| 5,868,707 A | 2/1999 | Williams et al. |

(Continued)

FOREIGN PATENT DOCUMENTS

EP 0589452 A1 3/1994

OTHER PUBLICATIONS

Extended European Search Report issued in corresponding European Application No. 21168100.2 dated Sep. 9, 2021, 7 pages.

(Continued)

*Primary Examiner* — Si Ming Ku
(74) *Attorney, Agent, or Firm* — Carter, DeLuca & Farrell LLP

(57) ABSTRACT

A surgical kit includes a cannula assembly and a sheath. The cannula assembly includes a housing, an elongate shaft defining a lumen and extending from the housing, a fluid port adapted to be coupled to a fluid source, and an expandable body in fluid communication with the fluid port. The sheath is configured to be disposed over the expandable body of the cannula assembly to apply a compressive force to the expandable body. The sheath is transitionable between a contracted configuration and an expanded configuration.

19 Claims, 3 Drawing Sheets

(56) References Cited

U.S. PATENT DOCUMENTS

| | | |
|---|---|---|
| 6,908,454 B2 | 6/2005 | McFarlane |
| 7,300,448 B2 | 11/2007 | Criscuolo et al. |
| 7,316,699 B2 | 1/2008 | McFarlane |
| 7,691,089 B2 | 4/2010 | Gresham |
| 7,744,617 B2 | 6/2010 | Lunsford et al. |
| 7,850,643 B1 * | 12/2010 | Pacetti ................. A61K 31/573 604/96.01 |
| 7,963,975 B2 | 6/2011 | Criscuolo |
| 2004/0093005 A1 | 5/2004 | Durcan |
| 2004/0138702 A1 | 7/2004 | Peartree et al. |
| 2005/0010238 A1 * | 1/2005 | Potter ................ A61M 39/0606 606/129 |
| 2005/0113856 A1 | 5/2005 | Epstein et al. |
| 2005/0165432 A1 | 7/2005 | Heinrich |
| 2006/0079918 A1 | 4/2006 | Creston |
| 2006/0106402 A1 | 5/2006 | McLucas |
| 2013/0338435 A1 * | 12/2013 | Shen .................... A61B 90/361 600/106 |
| 2014/0276945 A1 * | 9/2014 | Pravong ................ A61M 39/02 606/130 |
| 2019/0224448 A1 * | 7/2019 | Connors ............... A61M 25/10 |

OTHER PUBLICATIONS

European Office Action dated Feb. 1, 2023, issued in corresponding EP Application No. 21 168 100, 4 pages.

* cited by examiner

PROTECTIVE SHEATH FOR USE WITH A SURGICAL INSTRUMENT HAVING AN EXPANDABLE BODY

FIELD

The disclosure relates generally to surgical instruments, and more particularly, to a sheath configured to protect an expandable body of a surgical instrument.

BACKGROUND

Minimally invasive surgical procedures, including endoscopic, laparoscopic and arthroscopic procedures, have been used for introducing surgical instruments inside a patient and for viewing portions of the patient's anatomy. Forming a relatively small diameter, temporary pathway to the surgical site is a key feature of most minimally invasive surgical procedures. The most common method of providing such a pathway is by inserting a trocar assembly through the skin. The trocar assembly may include an expandable body configured to enhance securement of the trocar assembly to an opening in tissue.

Obturators are typically designed with a tip that may be used to form an opening through the abdominal wall. An obturator is inserted into a cannula, and then the combined obturator and cannula are together placed against the skin to be penetrated. In order to penetrate the skin, the distal end of the obturator engages the skin, which may or may not have been previously cut with a scalpel. The obturator is then used to penetrate the skin and access the body cavity. By applying pressure against the proximal end of the obturator, the tip of the obturator is forced though the skin and the underlying tissue layers until the cannula and obturator enter the body cavity. The obturator is then withdrawn. The cannula remains in place within the incision for use during the minimally invasive procedure.

Such surgical instruments may experience large pressure differential during, e.g., ethylene oxide (EtO) sterilization process or air freight. However, such surgical instruments are in sealed systems that do not equalize pressure under such large pressure differential, which may inflate the expandable bodies. Such large pressure differential may damage or stress the expandable bodies. Accordingly, there is a need for a device that effectively and safely protects the expandable bodies of surgical instruments during, e.g., sterilization and transport, of the surgical instruments.

SUMMARY

In accordance with the disclosure, a surgical kit includes a cannula assembly and a sheath. The cannula assembly includes a housing, an elongate shaft defining a lumen and extending from the housing, a fluid port adapted to be coupled to a fluid source, and an expandable body in fluid communication with the fluid port. The sheath is configured to be disposed over the expandable body of the cannula assembly to apply a compressive force to the expandable body. The sheath is transitionable between a contracted configuration and an expanded configuration.

In an aspect, the sheath may have a uniform diameter.

In another aspect, the sheath may have a uniform thickness.

In yet another aspect, the sheath may define a chamber configured to receive a distal end portion of the elongate shaft therein.

In an aspect, the chamber of the sheath may be tapered to frictionally engage a portion of the distal end portion of the elongate shaft.

In another aspect, the sheath may have a first closed end and an open second end.

In yet another aspect, the open second end may be proximal of the expandable body of the cannula assembly when the sheath is disposed over the expandable body.

In still yet another aspect, the sheath may be integrally or monolithically formed.

In still yet another aspect, the sheath may partially extend along the elongate shaft of the cannula assembly.

In an aspect, the sheath may be formed of translucent material.

In another aspect, the sheath may be formed of an elastomer.

In yet another aspect, the sheath may be releasably secured to the distal end portion of the elongate shaft.

In still yet another aspect, the expandable body of the cannula assembly may be disposed at the distal end portion of the elongate shaft.

In accordance with another aspect of the disclosure, a surgical kit includes a surgical instrument including an expandable body adapted to be coupled to a fluid source, and a sheath configured to receive the expandable body of the surgical instrument therein. The sheath is transitionable between a contracted configuration and an expanded configuration. The sheath is configured to apply a compressive force to the expandable body of the surgical instrument in an expanded state.

In an aspect, the sheath may be releasably secured with the surgical instrument.

In another aspect, the sheath may have a first closed end and an open second end.

In yet another aspect, the sheath may be integrally or monolithically formed.

In still yet another aspect, the sheath may be expandable radially outwards.

In an aspect, the sheath may be formed of an elastomer.

In another aspect, the expandable body of the surgical instrument may be configured to engage tissue in a sealing relation.

BRIEF DESCRIPTION OF DRAWINGS

A protective sheath for use with surgical instruments is disclosed herein with reference to the drawings, wherein.

DETAILED DESCRIPTION

Figure 1:
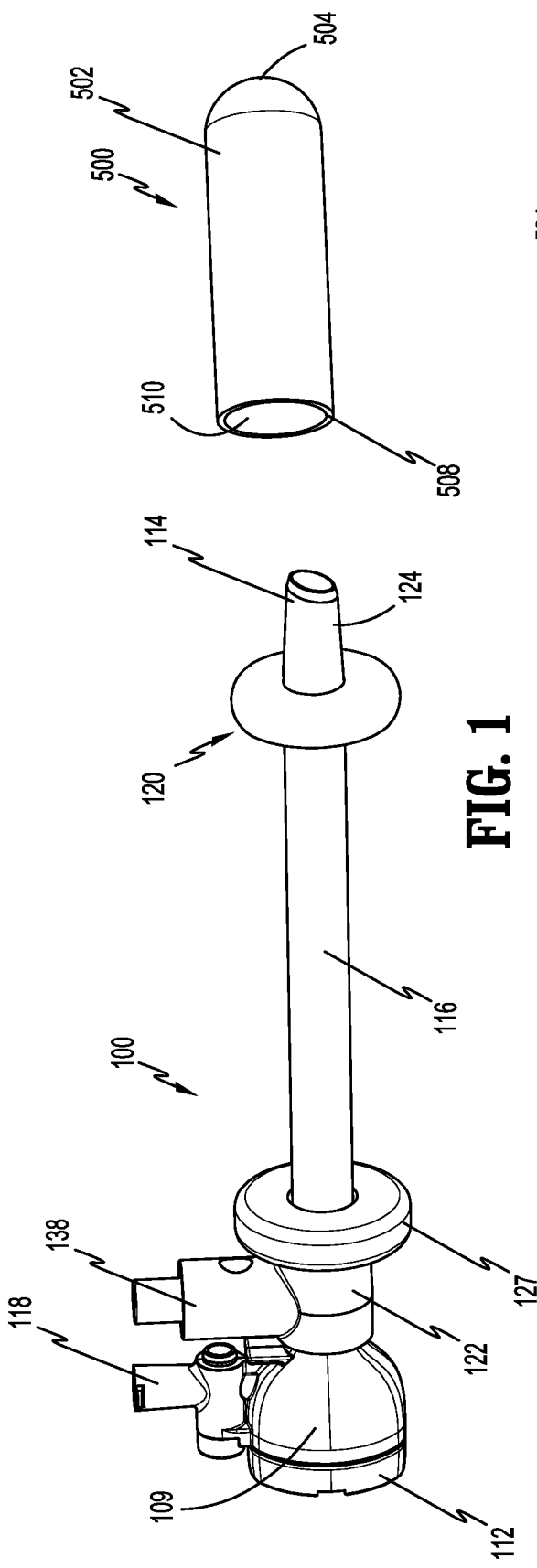
FIG. 1 is a perspective view of a surgical kit including a cannula assembly and a protective sheath in accordance with the disclosure.

A protective sheath for use with surgical instruments is described in detail with reference to the drawings, wherein like reference numerals designate corresponding elements in each of the several views. As used herein, the term "distal" refers to that portion of the instrument, or component thereof which is farther from the user while the term "proximal" refers to that portion of the instrument or component thereof which is closer to the user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 2:
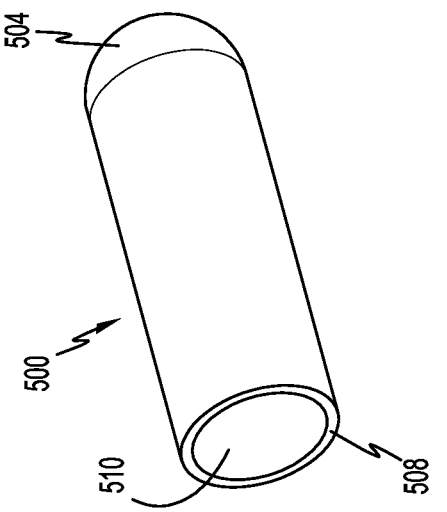
FIG. 2 is a partial perspective view of the surgical kit of FIG. 1.

With reference to FIGS. 1 and 2, a protective sheath for use with surgical instruments, in the form of a cannula assembly 100 is shown generally as 500. The protective sheath 500 is configured to provide compression force to an expandable body of the cannula assembly 100, while enabling the expandable body to expand, flex, and contract in size when the cannula assembly 100 experiences large pressure differential, e.g., during sterilization and transport, of the surgical instruments. Further, the protective sheath 500 may also protect a sterile barrier such as, e.g., a pouch, from damage by a distal end portion 124 of the cannula assembly 100. The cannula assembly 100 is configured to permit access to an insufflated abdominal cavity during a laparoscopic procedure to permit the introduction of a surgical object for performing various surgical tasks on internal organs within the cavity. The surgical object may be a surgical instrument such as laparoscopic or endoscopic clip appliers, obturators, graspers, dissectors, retractors, staplers, laser probes, photographic devices, tubes, endoscopes and laparoscopes, electro-surgical devices and the like. The cannula assembly 100 generally includes a cannula housing 112, a cannula member 114 extending from the cannula housing 112 and an outer sleeve 116 coaxially mounted over the cannula member 114, an expandable balloon 120, and a locking collar 127 positioned about a proximal end 122 of the cannula assembly 100 and advanceable to engage the exterior surface of tissue (e.g., the abdominal wall). The locking collar 127 in combination with the expandable balloon 120 minimizes movement of the cannula member 114 in both withdrawal and insertion directions and also assists in maintaining a seal about the passage in the abdominal wall.

The cannula housing 112 is dimensioned for engagement by the clinician and may include one or more internal seals 109 adapted to establish a seal about a surgical object introduced therethrough. The cannula housing 112 also may include an insufflation connector 118 (e.g., a luer connector) for connecting to a source of insufflation fluids (not shown) for delivery within, e.g., the abdominal cavity. A longitudinal lumen defined by the cannula member 114 is also in fluid communication with the insufflation connector 118 to convey insufflation fluids into the abdominal cavity to establish and/or maintain the pneumoperitoneum. The expandable balloon 120 is coupled to the outer sleeve 116. The cannula member 114 further includes a fluid port 138 positioned adjacent the cannula housing 112. The fluid port 138 is adapted to be coupled to a source of inflation fluids to inflate the expandable balloon 120. The outer sleeve 116 is coaxially mounted about the cannula member 114 and extends from a position within the fluid port 138 to a position adjacent the distal end portion 124 of the cannula member 114. The outer sleeve 116 may be secured within the fluid port 138 and to the cannula member 114 through a friction or interference fit or with the use of adhesives, cements or the like. The expandable balloon 120 is coupled to the outer sleeve 116 and is coaxially mounted about the distal end portion 124 of the cannula member 114. The expandable balloon 120 expands radially outwardly upon passage of inflation fluids through the fluid port 138.

With continued reference to FIGS. 1 and 2, the protective sheath 500 has an elongate body 502 having a closed first end portion 504 and an open second end portion 508. It is contemplated that the first end portion 504 may be open for internal examination and testing of cannula assembly components while the expandable balloon 120 is in the deflated state and protected by the protective sheath 500. The protective sheath 500 is detachably securable with the distal end portion 124 of the cannula member 114. The closed first end portion 504 may include an atraumatic tip. The protective sheath 500 may be integrally formed or, alternatively, monolithically formed. The protective sheath 500 is formed of a compliant material such as, e.g., elastomer. In an aspect, the protective sheath 500 may be formed of a translucent material. The protective sheath 500 defines a chamber 510 configured to receive the distal end portion 124 of the cannula assembly 100. For example, the chamber 510 may be tapered to frictionally engage a portion of the distal end portion 124 of the cannula assembly 100. The protective sheath 500 may include a uniform diameter and a uniform thickness. However, it is contemplated that the thickness and/or the diameter may vary along, e.g., a length, thereof. The protective sheath 500 has a length to ensure that the expandable balloon 120 of the cannula assembly 100 is disposed within the chamber 510. Thus, the open second end portion 508 of the protective sheath 500 may be disposed proximal of the expandable balloon 120 when the protective sheath 500 is placed about the expandable balloon 120.

Figure 3:
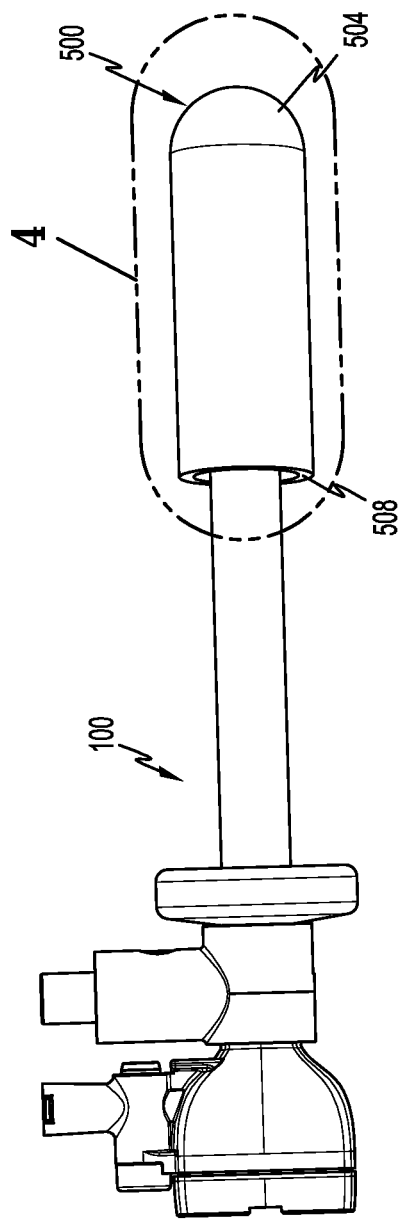
FIG. 3 is a perspective view of the surgical kit of FIG. 1, illustrating the protective sheath placed over an expandable balloon of the cannula assembly.
Figure 4:
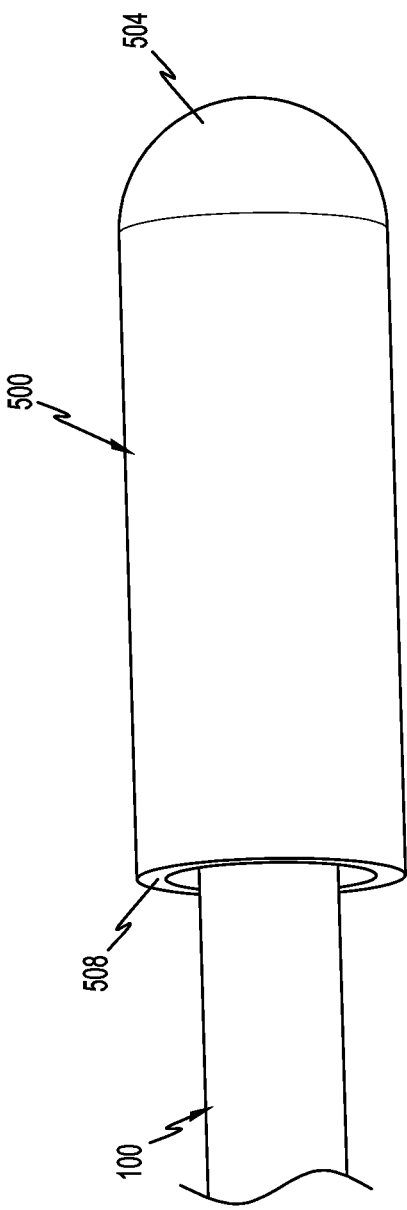
FIG. 4 is an enlarged view of the indicated area of detail of FIG. 3.
Figure 5:
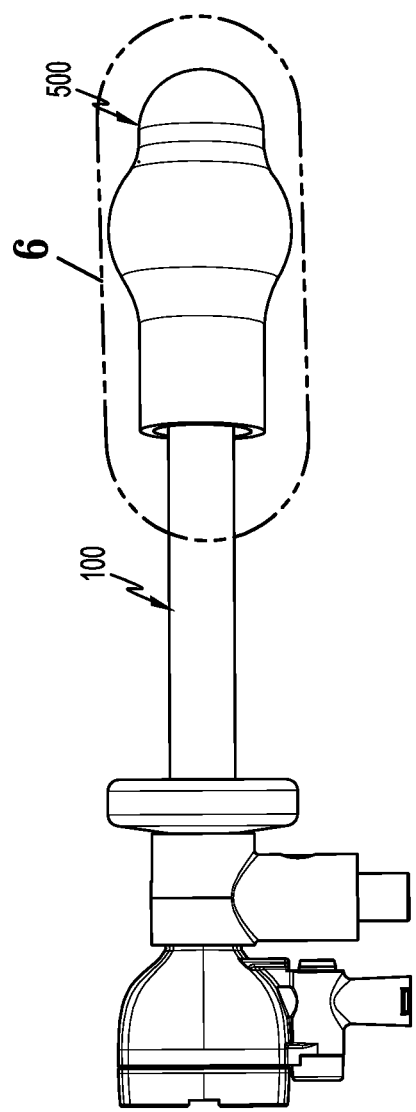
FIG. 5 is a perspective view of the surgical kit of FIG. 1, illustrating the protective sheath in an expanded configuration.
Figure 6:
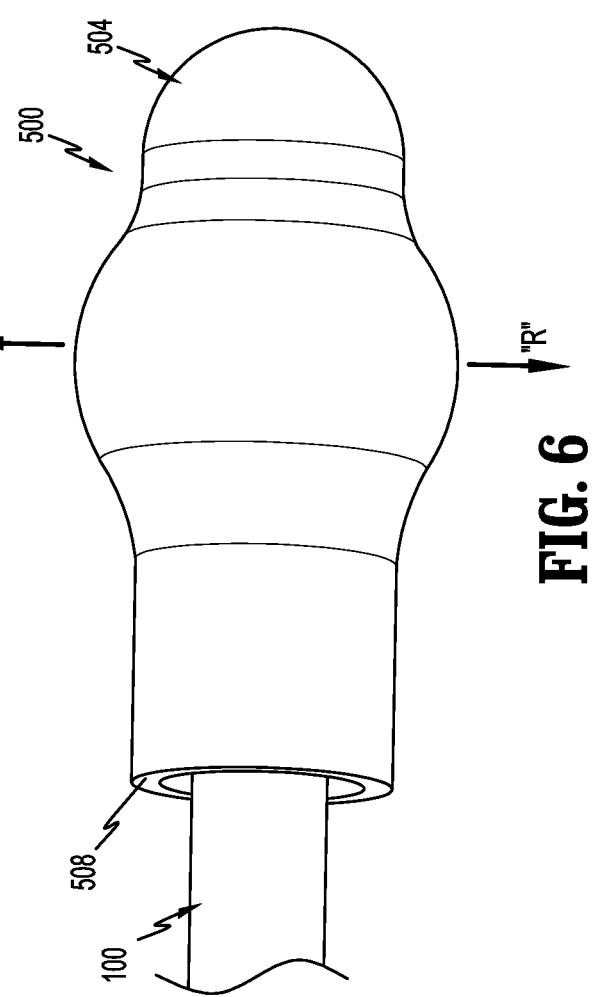
FIG. 6 is an enlarged view of the indicated area of detail of FIG. 5.

In use, the protective sheath 500 is placed over the distal end portion 124 of the cannula assembly 100 when the expandable balloon 120 is in the deflated state (FIGS. 3 and 4). In this manner, the expandable balloon 120 of the cannula assembly 100 is received within the chamber 510 of the protective sheath 500. Under such a configuration, when the cannula assembly 100 experiences large pressure differential, the expandable balloon 120 may expand radially outwards in the direction of arrows "R" (FIG. 6). The protective sheath 500 provides compressive force while enabling a predetermined amount of radial expansion of the expandable balloon 120 and the protective sheath 500 (FIGS. 5 and 6). The amount of radial expansion of the expandable balloon 120 and the protective sheath 500 may be controlled through the selection of the material, thickness, and configuration of the protective sheath 500. In this manner, the protective sheath 500 enables expansion and movement of the expandable balloon 120 therein, thereby reducing structural stress to the expandable balloon 120 and/or joints (e.g., welded or glued) connecting the expandable balloon 120 to the cannula member 114. The protective sheath 500 enables surgical instruments having an expandable body, such as the cannula assembly 100 to utilize EtO sterilization process which is a less expensive method of sterilization compared to other sterilization processes such as, e.g., gamma irradiation or E-beam sterilization processes. In addition, the protective sheath 500 also enables other methods of shipping, such as, e.g., air freight.

It is further contemplated that the cannula assembly may be used with an obturator (not shown). The obturator generally includes a head portion having latches configured to engage respective notches 117 defined in the cannula housing 112 of the cannula assembly 100 to enhance securement therewith, an elongate shaft extending from the head portion, and an optical penetrating tip coupled to a distal end of the elongate shaft. The optical penetrating tip may be used to penetrate the skin and access the body cavity. By applying pressure against the proximal end of the obturator, the tip of the obturator is forced though the skin and the underlying tissue layers until the cannula and obturator enter the body cavity. It is also envisioned that an inside surface of the protective sheath 500 may have longitudinal ribs configured to engage the expandable balloon 120 and to inhibit sliding or rotation for the protective sheath 500 relative to the cannula assembly 100 during shipping or sterilization process.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical kit comprising:
   a cannula assembly including a housing, an elongate shaft defining a lumen and extending from the housing, a fluid port adapted to be coupled to a fluid source, and an expandable body in fluid communication with the fluid port; and
   a sheath disposed over the expandable body of the cannula assembly to apply a compressive force to the expandable body during radial expansion of the expandable body of the cannula assembly, wherein the sheath is transitionable between a contracted configuration and an expanded configuration, the sheath formed of a gas permeable and compliant material such that the sheath disposed over the expandable body of the cannula assembly is expandable to enable a predetermined amount of radial expansion of the expandable body of the cannula assembly.

2. The surgical kit according to claim 1, wherein the sheath has a uniform diameter.

3. The surgical kit according to claim 1, wherein the sheath has a uniform thickness.

4. The surgical kit according to claim 1, wherein the sheath defines a chamber configured to receive a distal end portion of the elongate shaft therein.

5. The surgical kit according to claim 4, wherein the chamber of the sheath is tapered to frictionally engage a portion of the distal end portion of the elongate shaft.

6. The surgical kit according to claim 1, wherein the sheath has a closed distal end and an open proximal end that are disposed along a longitudinal axis of the sheath.

7. The surgical kit according to claim 6, wherein the open proximal end is proximal of the expandable body of the cannula assembly when the sheath is disposed over the expandable body.

8. The surgical kit according to claim 1, wherein the sheath is integrally or monolithically formed.

9. The surgical kit according to claim 1, wherein the sheath partially extends along the elongate shaft of the cannula assembly.

10. The surgical kit according to claim 1, wherein the sheath is formed of translucent material.

11. The surgical kit according to claim 1, wherein the sheath is formed of an elastomer.

12. The surgical kit according to claim 4, wherein the sheath is releasably secured with the distal end portion of the elongate shaft.

13. The surgical kit according to claim 4, wherein the expandable body of the cannula assembly is disposed in the distal end portion of the elongate shaft.

14. A surgical kit comprising:
    a surgical instrument including an expandable body adapted to be coupled to a fluid source; and
    a sheath removably disposed over the expandable body of the surgical instrument to apply a compressive force to the expandable body of the surgical instrument during transition of the expandable body of the surgical instrument to an expanded configuration from a contracted configuration, wherein the sheath is formed of a gas permeable and compliant material to enable a predetermined amount of radial expansion of the expandable body of the surgical instrument.

15. The surgical kit according to claim 14, wherein the sheath has a closed distal end and an open proximal end that are longitudinally spaced apart.

16. The surgical kit according to claim 14, wherein the sheath is integrally or monolithically formed.

17. The surgical kit according to claim 14, wherein the sheath is expandable radially outwards.

18. The surgical kit according to claim 14, wherein the sheath is formed of an elastomer.

19. The surgical kit according to claim 14, wherein the expandable body of the surgical instrument is configured to engage tissue in a sealing relation.

* * * * *